United States Patent [19]

de la Guardia et al.

[11] 4,314,572

[45] Feb. 9, 1982

[54] METHOD AND COMPOSITION FOR HAIR TREATMENT

[75] Inventors: Mario de la Guardia, Savannah, Ga.; Donald R. Cowsar, Birmingham, Ala.

[73] Assignee: Carson Products Company, Savannah, Ga.

[21] Appl. No.: 119,836

[22] Filed: Feb. 8, 1980

Related U.S. Application Data

[63] Continuation-in-part of Ser. No. 805,149, Jun. 9, 1977.

[51] Int. Cl.³ .............................................. A45D 7/00
[52] U.S. Cl. .......................................... 132/7; 424/70
[58] Field of Search ....................... 132/7; 424/70–72, 424/79, 161; 521/28

[56] References Cited

U.S. PATENT DOCUMENTS

| | | | |
|---|---|---|---|
| 2,684,321 | 7/1954 | Thurmon | 424/79 |
| 2,781,290 | 2/1957 | Martin | 424/79 |
| 2,836,543 | 5/1958 | Watson | 132/7 |
| 3,154,470 | 10/1964 | Braun | 424/161 |
| 3,242,052 | 3/1966 | Sheffiver | 132/7 |

Primary Examiner—G. E. McNeill
Attorney, Agent, or Firm—Newton, Hopkins & Ormsby

[57] ABSTRACT

A method and composition for curling hair and for straightening hair is disclosed, wherein the method involves the application of guanidine hydroxide to the hair. The guanidine hydroxide is prepared by mixing together in an aqueous medium at least one water-soluble guanidine salt and at least one particulate, strong-base, quaternary ammonium, hydroxide-form ion-exchange resin. After the mixed components have had a chance to undergo ion exchange, to form an aqueous solution of guanidine hydroxide, the guanidine hydroxide composition is separated from the ion-exchange resin, and applied to the hair withinin 48 hours. The treatment with guanidine hydroxide causes the hair to maintain a desired configuration by conducting the treatment with the hair in the desired configuration during at least a portion of the time that the hair is in contact with the guanidine hydroxide solution.

14 Claims, No Drawings

METHOD AND COMPOSITION FOR HAIR TREATMENT

CROSS REFERENCE TO RELATED APPLICATION

This application is a continuation-in-part of co-pending application Ser. No. 805,149 filed by Mario de la Guardia on June 9, 1977.

SUMMARY OF THE INVENTION

The present invention is based on the discovery that guanidine hydroxide-based effective human hair straightening or relaxing compositions, or human hair permanent wave composition, can be prepared by mixing together in an aqueous medium at least one water-soluble guanidine salt and at least one particulate, strong-base, quaternary ammonium, hydroxide-form ion-exchange resin. The resin should have an affinity for the anion of the guanidine salt which is at least equal to the affinity of the resin for the hydroxyl ion. Guanidine hydroxide is produced by mixing the resin and the guanidine salt together, and allowing the ion exchange reaction to progress. After the ion exchange reaction is substantially complete, which is normally determined as the time at which pH equilibrium is achieved, the aqueous solution of guanidine hydroxide can be separated from the ion-exchange resin, applied to hair, allowed to maintain contact with the hair for an effective time, and then removed from the hair.

BACKGROUND OF THE INVENTION

Commercial products based upon compositions containing thioglycolates, sulfites or alkali metal hydroxides, such as sodium hydroxides, have been widely used to permanently straighten unstraight hair, especially to straighten unstraight Negro hair. Of these products, the thioglycolate compositions and the sulfite compositions which have been commercially marketed have been relatively ineffective, with the hair in many cases reverting at least partially to the original unstraight form. While very effective in producing the desired straightening effect, sodium hydroxide compositions are very harsh to both the scalp and the hair, and the use of such compositions has resulted in numerous instances of scalp irritation and/or burning, and has also resulted in a substantial reduction of the strength of the treated hair, and even, in some instances, considerable hair loss.

Various guanidine compounds have been evaluated by the prior art in hair waving or hair straightening compositions. Of these guanidine thioglycolate appears to have had the most attention by researchers in this art. See, for example, Shansky, *American Perfumer and Cosmetics*, Volume 78, August, 1963, 32–34; Bogaty et al, *American Perfumer and Cosmetics*, Volume 78, November, 1963, pages 45–47; and Shansky, *American Perfumer and Cosmetics*, Volume 78, December, 1963, pages 29–30.

Various organic bases including guanidine have been found to accelerate the dehairing effect of calcium hydroxide suspensions. See, e.g. Barry, "Delipatories" *Cosmetic Science and Technology*, Edited by Balsam and Sagarin, 2nd Edition, Volume 2, Chapter 18, page 39, 45, Wiley Interscience, New York, 1972 and Barry "Depilatories" *Cosmetic Science and Technology*, Edited by Sagarin, First Edition, Chapter 20, page 461–462, Interscience Publishers, New York, 1957, and references cited therein.

The co-pending application of Mario de la Guardia, Ser. No. 805,149, filed June 9, 1977, discloses that guanidine hydroxide is an effective human hair straightening or relaxing composition, as well as an effective permanent wave composition. The compositions exhibit improved hair strength retention and significantly reduce scalp irritation, compared to hair relaxing compositions based on alkali metal hydroxides. The permanent relaxation effect is generally as good as that achieved by the use of alkali metal hydroxides (such as sodium hydroxide).

U.S. Pat. No. 3,157,578, Nov. 17, 1964, discloses compositions for the permanent waving of human hair utilizing a solution containing, e.g. thioglycollic acid and guanidine carbonate. These compositions are employed in the form of aqueous solutions having a pH value of from 7–9, with the guanidine used to replace ammonia used previously thereto, both to function as a neutralizing agent for the acid reducing agent, and also in the form of ammonium carbonate for pH control.

U.S. Pat. No. 3,861,868 of Jan. 21, 1975 acknowledges, in column 1 thereof, earlier abandoned applications relating to the use of guanidine salts in hair dying compositions and hair bleaching compositions.

British Pat. No. 1,274,565 of May 17, 1972 discloses a process for the straightening of human hair wherein the hair straightening is conducted in two separate stages. In the first stage, a known keratin softening substance, such as an alkali hydroxide, sulfite or bisulfite, or a salt of a mercaptocarboxylic acid, is permitted to act upon the hair. After the extensive removal of the keratin softening component, a media containing a swelling substance is applied to the hair. Suitable swelling agents include monovalent aliphatic alcohol, aromatic alcohols, aliphatic diols, ether alcohols, sulfoxides, sulfones, thiocyanates, thiourea and urea, and water-soluble derivatives thereof.

U.S. Pat. No. 3,865,930 of Feb. 11, 1975 discloses a permanent wave composition based on a two-stage operation, wherein in the first stage the S-S linkages of the keratin fiber are opened at an alkaline pH with the addition of a reducing agent such as a thiol. The hair is then treated in a second stage with an oxidizing or neutralizing agent to reconstitute the S-S bridges, so as to impart to the hair the desired configuration. The patent relates to a composition for the aforesaid second stage, wherein the S-S bridges are reformed. This composition is a two-component composition, with one component based on a water-soluble sulfite, bisulfite, metabisulfite or thiourea, and the other component is hydrogen peroxide.

U.S. Pat. Nos. 2,817,342 of Dec. 24, 1957 and 2,840,086 of June 24, 1958 relate to permanent waving compositions based upon sulfite-type materials. Among other acid sulfites disclosed are an acid solution of guanidine bisulfite, formed by bubbling sulfur dioxide gas into an aqueous solution of guanidine carbonate.

Japanese Pat. No. 76-9013 discloses hair waving or straightening treatments wherein the hair is initially treated with a weak alkali, followed by a treatment with a chelating metallic salt solution. Calcium oxide or calcium hydroxide is used as a chelating agent to prevent mutual interactions of the active ingredients.

U.S. Pat. No. 2,836,543 of May 27, 1954 discloses the use of guanidine as a swelling agent component in a hair setting composition. The composition also includes a water-soluble sulfite and a polyfunctional aromatic additive compound, such as genetistic acid, which acts as an accelerator.

U.S. Pat. No. 3,642,429 of Feb. 15, 1972 is directed to a hair treatment composition based on a polycondensate of methylol compounds and an urein compound. The generic formula for the urein compound appears to encompass guanidine, but guanidine is not named in that patent.

U.S. Pat. No. 3,686,296 is directed to depilatories which are nitrogen-based thioglycerol molecular complexes. The nitrogen base may be, e.g. guanidine or guanidine hydrochloride.

DETAILED DESCRIPTION OF THE INVENTION

The parent application, Serial No. 805,149, discloses and claims a method for treating hair to cause the hair to maintain a desired configuration. The hair is contacted for an effective time with an effective amount of an aqueous composition comprising guanidine hydroxide as the principal active ingredient of the composition, and then the composition is removed from the hair.

According to the present invention, the guanidine hydroxide aqueous solution is produced by mixing together in an aqueous medium at least one water-soluble guanidine salt in a concentration greater than 0.25 molar in guanidine, and an effective amount of at least one granular, strong-base, quaternary ammonium, hydroxide-form, ion-exchange resin. The ion-exchange resin must have an affinity for the anion of the guanidine salt which is at least equal to the affinity of the resin for the hydroxyl ion, and preferably has a greater affinity for the anion of the guanidine salt than for the hydroxyl ion. The guanidine salt and the ion-exchange resin are allowed to remain in contact in the aqueous medium for at least 1 minute, preferably at least 2 minutes, to produce an aqueous solution of guanidine hydroxide. The ion-exchange resin is separated from the guanidine hydroxide solution, producing a guanidine hydroxide solution substantially free of ion-exchange resin. The guanidine hydroxide solution so produced is suitable for use directly on human hair, preferably after the addition of conventional additives thereto, such as thickeners, emulsifiers and the like.

The ion-exchange resins which are useful in the present invention are strong-base, quaternary ammonium, hydroxide-form ion-exchange resins. These resins must be in their hydroxyl form to be useful in the present invention. It is preferred that the resin be one exhibiting maximum basicity and exchange capacity. The resin should have an exchange capacity of at least 3.0 meq/g, preferably at least 3.5 meq/g, more preferably at least 4.0 meq/q. The degree of cross linking in the resin is not critical to the present invention, except to the extent that cross linking may affect other criteria.

Commercially available ion-exchange resins which may be used in the present invention are Duolite A-100 D, A-104 and A-102 D, products of Diamond Shamrock Corporation, Amberlite-IRA-400, -IRA-402, -IRA-420, as well as Amberlite CG-400 type II and type III, products of Rohm and Haas, and Dowex 1×1, 1×2, 1×4, products of Dow Chemical Company. With most of the above resins, 40 to 50 grams of the resin will be required in order to get conversion of the guanidine salt to guanidine hydroxide. With resins having even higher exchange capacities, however, the amount of resin used can of course be less than indicated above. Normally, however, at least 40 grams of the resin will be utilized. Greater amounts of the resin can be used without adverse effect, from a technical viewpoint, but will add substantially to the cost of the resulting system. The amount of resin used must be at least that amount required to exchange enough anions of the guanidine salt for hydroxyl groups, in order to produce enough guanidine hydroxide to be effective in the treatment of hair, as explained hereinafter.

For resins which are used in the method of the present invention, it is preferred that the resin be of a mesh size (U.S. standard screen size) which is at least 60 mesh, and preferably is larger than 60 mesh in size. This large resin particle size aids in separation of the resin from the aqueous guanidine hydroxide solution.

The guanidine salt which is used in the method of the present invention must be water-soluble to an extent that an aqeuous solution of the guanidine salt can be prepared having a concentration greater than 0.25 molar in guanidine. A large number of guanidine salts can be utilized, but the salt anion and the particular ion-exchange resin must be chosen such that the affinity of the counter ion for the resin must be equal to or greater than the affinity of the resin for the hydroxide ion, so that a conversion of a substantial amount of the guanidine salt to the hydroxide will be achieved when the aqueous guanidine salt solution is mixed with the hydroxide-form ion-exchange resin. The most preferred guanidine salt is guanidine sulfate, but other guanidine salts which are preferred include the nitrate, the tartrate, the oxalate and the carbonate. Less preferred but operable guanidine salts include the hydrochloride, the sulfite, the phosphate, the fluoride and, as an even less preferred embodiment, the laurate. Guanidine acetate can be utilized, and in general guanidine salts of alkane and alkene carboxylic acids having from 2 to 20 or more carbon atoms can be utilized. The divalent acids are preferred, among the various organic acids. In addition to the salts listed above, guanidine bicarbonate, bisulfite, or bisulfate as well as guanidine thioglycolate and guanidine alginate, could be used, but are not preferred. Normally the ion-exchange resin and the guanidine salt will be mixed together at substantially ambient conditions, although elevated or reduced temperatures could be utilized if desired. Normally, however, the reaction temperature will be no lower than 35° F., and no higher than 140° F., as no advantage will be gained by working outside of this range.

After the two components have been admixed together in an aqueous system, the resulting guanidine hydroxide solution should be used within about 48 hours, due to the relative instability of the guanidine hydroxide solution when exposed to ambient conditions. The guanidine hydroxide in the aqueous guanidine hydroxide solution tends to be converted into guanidine carbonate upon exposure to atmospheric carbon dioxide, and the guanidine carbonate is inactive as a hair treating agent according to the method of the present invention.

Higher concentrations of guanidine hydroxide in the hair treating composition raise the possibility of greater scalp irritation and more hair damage. The treatment time can generally be reduced with such higher concentrations, so that if adequate care is taken, as may be the case in commercial beauty shop operations, to minimize exposure, such high concentrations may be utilized. In general, the amount of guanidine hydroxide in the relaxer compsition can vary from about 1% by weight to about 50% by weight, based on the total weight of guanidine hydroxide plus water and conventional additives, if any, present. Concentrations below about 1% by weight are generally too dilute to be effective, and concentrations of guanidine hydroxide in the solution above about 50% by weight generally exceed the solubility limit. It is greatly preferred that the guanidine hydroxide concentration in the solution be within the range of 2 to 20% by weight, based on the total weight of the composition. More preferably, the guanidine hydroxide concentration is in the range of 3-10% by weight, based on the total weight of the solution, and more preferably the guanidine hydroxide concentration is from 4 to 7% by weight, based on the total weight of the solution.

Enough ion-exchange resin must be used such that the exchange capacity of the amount of resin used is sufficient to convert enough guanidine salt in the solution into guanidine hydroxide, within the abovenoted concentration ranges.

There is no importance in the order of mixing of the water, the guanidine salt, the ion-exchange resin, and any conventional additives in the system. Normally, however, it is simplest to prepare an aqueous solution of the guanidine salt, with the other additives contained therein, and then add that solution to the ion-exchange resin. The guanidine salt will preferably be in the form of an aqueous solution having at most about 40% by weight of the guanidine salt, preferably less than 35% by weight of the guanidine salt, and generally having at least about 1.2% by weight of the guanidine salt. An increase or decrease in the concentration of one component of the system may be compensated by an appropriate adjustment to the concentration of the other ingredient, and to the ratio of the two ingredients in the system. The important item, however, is the concentration of the resulting guanidine hydroxide in the guanidine hydroxide solution, and that concentration should be within the ranges set forth above. As applied to the hair, the relaxer composition of the present invention will not contain any sulfur-based keratin-breaking agents, and preferably the active components of the system do not contain, as applied to the hair, any organic sulfur-containing compounds. Thiourea may be utilized as an accelerator, but this is normally unnecessary and is not preferred. Sulfur-containing compounds may be in the initial mixture of guanidine salt and ion-exchange resin, such as, for instance, guanidine sulfate or guanidine sulfite or their bisulfate and bisulfite analogues. These compounds, however, would not be active ingredients in treating hair per se, and the sulfate and/or sulfite ions would be bound to the ion-exchange resin, to the extent of the resin exchange capacity, and in that form would certainly not be an active agent in the hair treatment. Thus, the system and method of the present invention can be readily distinguished from prior art compositions and methods based upon thioglycolates or sulfites as active ingredients.

The guanidine hydroxide aqueous solution-based system which is applied to the hair according to the method of the present invention should have a relatively high pH. The pH value of the guanidine hydroxide solution is generally above 11.8, preferably about 12.5 to about 13.5, and most preferably around 13.0.

Normally an excess of the ion-exchange resin will be utilized, as an excess of the guanidine salt will frequently reduce the pH of the resulting mixture, to the point that the guanidine hydroxide may not act efficiently to treat hair. For the most efficient ion exchange systems, the mole ratio would theoretically be 1:1, but this condition is difficult to achieve, and normally the ion exchange ratio will be within the range of 1:2-1:3 of guanidine salt:ion-exchange resin. The ratio may be as high as 1:7.5, or even as high as 1:10, but for commercial embodiments it is anticipated that the ratio will be within the aforesaid preferred range.

Conventional additives may be present in the systems of the present invention in order to provide their known functions therein. For instance, the guanidine salt may be in an aqueous cream component, which can contain an emulsifier, a thickener, an emollient, and/or a humectant. Preservatives may be added to the system, and accelerators may also be present, especially if low concentrations of guanidine hydroxide are utilized.

When conventional additives are present in the guanidine hydroxide aqueous solution, it is preferred that they be added to the guanidine hydroxide solution after separation of the ion-exchange resin therefrom. Thus, the presence of the conventional additives will not interfere with the ion exchange reaction. Certain of these additives, however, may be added to the guanidine salt before ion exchange reaction, or may be added to the mixture of the guanidine salt and ion-exchange resin during the time that the ion exchange reaction is proceeding.

It is preferred to utilize a system which achieves an equilibrium pH within 1-2 minutes of mixing, to insure that the ion exchange reaction is substantially complete.

Thorough mixing of the ingredients of the system, especially when a cream or emulsion is utilized, is strongly recommended. The ion exchange reaction between the ion-exchange resin and the guanidine salt generally proceeds relatively rapidly upon adequate mixing, and normally is substantially complete within a few minutes time. For some systems, the ion exchange reaction will be substantially complete within one minute or so, and in the preferred system the ion exchange reaction will be completed within two minutes or so. For some systems, however, additional time for the ion exchange reaction to proceed must be allowed, and times as long as five or even ten minutes may be indicated for particular systems of particular ion-exchange resins and guanidine salts. A rough indication of the amount of time required can be obtained by measuring the time for a given mix system to reach an equilibrium pH. Such an equilibrium pH is achieved when the pH of the mixed system remains substantially constand for several minutes. The time at which such pH is first reached can be readily determined, by use of a monitoring pH probe, and the time at which such pH is first achieved can be considered the equilibrium pH time.

While creams or emulsions may be used in some instances, for certain guanidine salts, such as guanidine alginate, the salt itself may have sufficient thickening ability that other thickeners or emulsifiers are unnecessary.

The use of guanidine hydroxide as a hair treating agent, for straightening or relaxing hair, or for curling hair, is disclosed in the co-pending application of Mario de la Guardia, Ser. No. 805,149, which is hereby incorporated by reference for such teachings.

The time of treatment of hair which is to be treated according to the present invention, with the system of the present invention, will normally be within the range of 5 to 45 minutes, with the time starting from the first application of the system to the hair. Normally this treatment time will be at least 10 minutes, and there is no real upper limit on the time that the system can remain on the hair, with the above-noted 45 minute time generally being about the greatest length of time that is acceptable to end users. It is greatly preferred to utilize a treatment time of no more than about 30 minutes, and preferably less than about 25 minutes. Most preferably the treatment time will be in the neighborhood of about 20 minutes or so.

After the above treatment time has elapsed, the remaining guanidine hydroxide solution should be removed from the hair in order to prevent further decrease of the strength retention of the treated hair. A major portion of the guanidine hydroxide composition can be removed from the hair by thorough rinsing. It is preferred that the rinsing step be followed by a neutralizing step, using any suitable neutralizing agent. A buffered neutralizing shampoo has been found to be effective, but any conventional neutralizing methods and compositions, well known to the art, may be utilized. For instance, citric acid may be added to a conventional shampoo until the pH of the acidified shampoo has been reduced to 5.0 or so to form an effective neutralizing shampoo. Preferably the hair is neutralized by reducing the pH thereof to a value of no greater than about 7, and more preferably to a value of about 5.0-6.5. While lower pH values may be used, it is generally preferred to maintain the pH of the treated hair within the range of about 5.0 to about 7.0.

Generally the composition will be applied to the hair at ambient temperatures, but the composition may be at a temperature of say 35°-140° F. if desired. No advantages will be obtained by working outside of this temperature range.

The commercial hair curling compositions now on the U.S. market appear to be based on ammonium thioglycolate or sodium sulfite and/or ammonium sulfite. These compositions produce a decidedly unpleasant odor of mercaptans, ammonia and/or sulfur dioxide. In addition to the advantages described hereinabove, another decided advantage of the system of the present invention, when used for curling applications, is freedom from such objectionable odors.

The guanidine hydroxide solution may be applied to the hair by various means, depending upon the viscosity of the guanidine hydroxide solution. Suitable methods are disclosed in the aforesaid parent application Ser. No. 805,149.

EXAMPLES OF THE INVENTION

EXAMPLE 1

Duolite A-104, a benzyltrimethylammonium chloride ion-exchange resin manufactured by Diamond Shamrock, having a rated salt splitting capacity of 3.5 meq/g, was placed in a 1 liter beaker having a magnetic stirrer. The approximately 600 g of resin were washed with 1 N hydrochloric acid, filtered, rinsed several times with deionized water and then washed with a 1 N sodium hydroxide solution to convert the chloride ions on the resin to hydroxide ions. The beaker was decanted and the degree of conversion checked by adding silver nitrate to the decanate (a precipitate indicates that chloride ions are still being removed from the resin). After the ion exchange reaction was complete, the beaker was decanted and the resin contained therein washed with deionized water.

A guanidine hydrochloride solution having a pH of approximately 7 was formed by dissolving 23.21 g of guanidine hydrochloride in 500 ml of deionized water. About 300 ml of the ion-exchange resin prepared above, having an apparent density of 720-750 g per liter, was placed in a beaker and covered with guanidine hydrochloride solution. After stirring 30 minutes at room temperature, the beaker contents were decanted, with the decantate product having a pH of 12.7-12.8. The decantate product was checked for the presence of chloride ions and no such ions were present.

Ten weight percent of cetomacrogol wax emulsifier, and 2.5 weight percent of cetyl alcohol thickener were added to the decantage product, in an aqueous solution of guanidine hydroxide, and then the resulting composition was applied to medium-to-fine texture brown virgin hairs. Ten hairs were wrapped on a 5 mm diameter glass rod and retained on the rod with tape and rubber bands. The composition was applied to the wound hairs by a spatula. The composition was allowed to contact the hairs for 15 minutes and then the formulation was removed by rinsing from the hairs using warm tap water for 2 minutes. The treated hairs were neutralized to a pH of 6.4-6.5, again rinsed in warm tap water and blow dried for 5 minutes with a hair dryer. The hairs were removed from the glass rod by cutting in order to avoid any straightening of the curls, and allowed to remain at ambient conditions for 18 hours, after which the curls were measured for curl diameter and hair length. The treated hairs had a smaller curl diameter and a shorter length than the control, which were hairs treated with thickened deionized water.

EXAMPLE 2

Guanidine hydroxide was prepared following the general procedures of Example 1, to produce an aqueous solution containing 5 percent by weight of guanidine hydroxide.

About 20-25 medium texture, kinky Negro hairs were clamped in a straightened position on a glass rod and then immersed into a beaker containing the guanidine hydroxide solution at room temperature. Two different tests were conducted, at 20 and 30 minutes immersion time. The guanidine hydroxide was rinsed from the hairs using warm tap water for 2 minutes, and then the rinsed hairs were neutralized to a pH of 6.4-6.5, rinsed again and blow dried. Upon removal of the clamps, a noticeable increase was observed in the straightening effect which was obtained in each test, as compared to a control test wherein the hairs were immersed in deionized water.

EXAMPLES 3-15

These examples relate to the production of guanidine hydroxide by ion exchange with a number of different guanidine salts. The ion-exchange resin utilized in these examples was Duolite A-104, having a rated exchange capacity of 3.5 meq/g, and an actual, measured exchange capacity of 3.1 meq/g. The Duolite A-104 had a particle size of 40 mesh. In these examples, the guanidine salts listed were utilized in an amount corresponding to 0.00348 mols of guanidine. The appropriate amount of guanidine salt was dissolved in 10 ml of water (with the exception of the guanidine laurate, wherein 15 ml of water was used) and then the resulting guanidine salt solution was added to the Duolite A-104 resin, with the resin also having 10 ml of water added thereto prior to the guanidine salt solution addition. The amount of resin used was that required to produce the indicated mol equivalent ratios. Before the guanidine salt solutions were added to the resin, they were titrated to a pH of 8, so that equal starting pHs were utilized. The resins were titrated with either guanidine hydroxide, when their pH was less than 8, or with an acid corresponding to the guanidine salt anion, when the pH was greater than 8. In every instance except for the use of sodium alginate (which produced a gel), the resin/guanidine salt mixture was stirred.

The table set forth below gives the results of making guanidine hydroxide solutions according to these examples.

| Example | Guanidine Salt | Mole Equivalent Ratio, Salt:Resin | Final Measured pH | Time to Reach pH equilibrium, minutes |
|---|---|---|---|---|
| 3 | Sulfate | 1:6.6 | 13.50 | 2 |
| 4 | Carbonate | 1:5.6 | 12.95 | 2 |
| 5 | Hydrochloride | 1:7.7 | 13.30 | 1 |
| 6 | Nitrate | 1:6.6 | 13.30 | 2 |
| 7 | Tartrate | 1:6.3 | 13.30 | 1 |
| 8 | Sulfite | 1:6.5 | 13.25 | 1 |
| 9 | Laurate | 1:6.6 | 12.80 | 8 |
| 10 | Phosphate | 1:7.6 | 13.10 | 3 |
| 11 | Fluoride | 1:7.5 | 12.95 | 2 |
| 12 | Oxalate | 1:6.5 | 13.30 | 1 |
| 13 | Thioglycolate | 1:7.2 | 12.95 | 5 |
| 14 | Acetate | 1:7.2 | 12.85 | 2 |
| 15 | Alginate | 1:6.8 | 12.58 | 2 |

All of the guanidine hydroxide solutions produced by the above ion exchange reactions would effectively straighten or relax kinky Negro hairs, following the procedures of Example 2.

What is claimed is:

1. An improvement in a method for treating hair of the type wherein a composition comprising guanidine hydroxide is applied to the hair and is subsequently removed therefrom, the improvement comprising the steps of:
    (a) providing a first ingredient comprising a guanidine salt;
    (b) providing a second ingredient comprising a quaternary ammonium, hydroxide-form, ion exchange resin;
    (c) mixing said first ingredient and said second ingredient so as to produce guanidine hydroxide; and
    (d) separating said guanidine hydroxide from said resin.

2. Method of claim 1, wherein said guanidine salt is selected from the group consisting of guanidine sulfate, carbonate, hydrochloride, nitrate, sulfite, phosphate, fluoride, oxalate, thioglycolate and alginate and guanidine carboxylic acid salts of alkane and alkene carboxylic acids having from 2 to about 20 carbon atoms.

3. Method of claim 1, wherein said guanidine salt and said ion-exchange resin are mixed together at a temperature of about 5° to about 95° C.

4. Method of claim 1, wherein said guanidine salt and said ion-exchange resin remain in contact in said aqueous medium for at least 2 minutes.

5. Method of claim 1, wherein the concentration of said guanidine salt is 0.25 molar.

6. Method of claim 2, wherein said ion-exchange resin has a particle size of 60 mesh or larger.

7. Method of claim 6, wherein said resin has a salt splitting capacity of at least about 3.0 meq/g.

8. Method of claim 7, wherein said salt splitting capacity is at least about 3.5 meq/g.

9. Method of claim 7, wherein at least 40 grams of resin are used to treat each adult head of hair.

10. Method of claim 9, wherein at least 50 grams of said resin are used for each adult head of hair.

11. A method for treating hair, comprising the steps of:
    (a) mixing a first ingredient comprising a guanidine salt having a concentration of 0.25 molar and selected from the group consisting of guanidine sulfate, nitrate, tartrate, oxalate, carbonate, phosphate, laurate, acetate, bisulfate, bisulfite, alginate, hydrochloride, sulfite, flouride, and alkane and alkene carboxylic acids having from 2 to at least 20 carbon atoms, with a second ingredient comprising a quarternary ammonium, hydroxide-form, ion exchange resin so as to form guanidine hydroxide;
    (b) separating said guanidine hydroxide from said resin;
    (c) applying said guanidine hydroxide to said hair for a selected period of time; and
    (d) removing said guanidine hydroxide from said hair.

12. A composition for treating hair, comprising a guanidine salt ingredient and a quarternary ammonium, hydroxide-form, ion exchange resin ingredient, said ingredients being selected such that the reaction product thereof comprises quanidine hydroxide which is separated from said ion exchange resin ingredient and applied to said hair.

13. A composition of claim 12, wherein said guanidine salt ingredient is selected from the group consisting of guanidine sulfate, nitrate, tartrate, oxalate, carbonate, phosphate, laurate, acetate, bisulfate, bisulfite, alginate, hydrochloride, sulfite, flouride and alkane and alkene carboxylic acids having from 2 to at least 20 carbon atoms.

14. A composition of claim 12, wherein the concentration of said guanidine salt ingredient is 0.25 molar.

* * * * *